United States Patent [19]

Saimoto et al.

[11] Patent Number: 5,084,388
[45] Date of Patent: Jan. 28, 1992

[54] METHOD OF PRODUCING BRASSINOSTEROIDS

[75] Inventors: Hiroshi Saimoto, Misato; Masako Otsuka, Soka; Mifumi Yamamoto, Koshigaya; Masao Kawashima, Warabi; Shozo Fujioka, Kamifukuoka; Akira Sakurai; Takao Yokota, both of Tokyo; Kunihiko Shono, Fujisawa, all of Japan

[73] Assignees: Somar Corporation and The Institute of Physical and Chemical Research, both of; The Institute of Physical and Chemical Research, Japan

[21] Appl. No.: 629,609

[22] Filed: Dec. 18, 1990

[30] Foreign Application Priority Data

Dec. 19, 1989 [JP] Japan .................................. 1-330030

[51] Int. Cl.⁵ .................. C12P 33/00; C12P 33/20; C12P 17/08; C12N 13/00
[52] U.S. Cl. ..................................... 435/124; 435/52; 435/53; 435/173
[58] Field of Search .................... 435/52, 53, 124, 173; 549/268

[56] References Cited

U.S. PATENT DOCUMENTS 3,628,287 12/1971 Staba et al. .
4,241,536 12/1980 Saint-Firmin .

OTHER PUBLICATIONS

JPOABS 01-269500, Sakurai et al., 10-26-89.
Derwent Abs. 89-360303/49, J01269500, Rikagak.
Online Database WPI Denvent Accession No. 89-360303, Abstract Agric. Biol. Chem., vol. 53, No. 3, 1989, pp. 805-811.

Primary Examiner—Herbert J. Lilling

[57] ABSTRACT

A method of producing a brassinosteroid is disclosed, wherein crown gall cells capable of producing the brassinosteroid are cultured in a culture medium in the presence of a cultivation aid selected from auxins, sterols, squalene, casamino acid and mixtures thereof.

11 Claims, No Drawings

METHOD OF PRODUCING BRASSINOSTEROIDS

This invention relates to a method of producing brassinosteroids by culturing plant cells.

Brassinosteroids which are steroidal plant growth hormones are found in a wide variety of higher plants and have thus far been isolated from various parts, such as pollen, seed, immatured seed, fruit, stem, leaf, shoot and flower, of various plant species such as *Brassica napus, Castanea crenata, Thea sinensis, Dystylium racemosum, Dolichos lablab, Phaseolus vuigaris, Oryza sativa* and *Zea mays*. "*Brassinosteroid*" *is a general term of brassinolide and its homologues:* Currently known are 22 kinds of brassinosteroids inclusive of naturally occurring and synthetic ones such as 25-methylcastasterone, homobrassinolide and 25-methylbrassinolide.

Numerous studies have been made on physiological activity of brassinosteroids to agricultural products. It has now been revealed that brassinosteroids exhibit growth promoting effects to wheat, corn, cucumber and pea, and to improve cool weather resistance of rice, cucumber and eggplant, disease resistance of Chinese cabbage and chemical and salt tolerance of various plants ("Chemistry and Biology" 23, 717(1985)).

Also made are extensive studies on chemical synthesis of brassinosteroids. Known methods, however, are complicated and require highly sophisticated techniques and cannot give the desired product with satisfactory yield and purity.

One known biological method for the production of brassinosteroids includes a step of culturing crown gall cells from a dicotyledon and a step of isolating the desired brassinosteroid or brassinosteroids from the culture (Japanese Published Unexamined Patent Application No. Hei-1-269500). In this method, however, the yield of the desired brassinosteroids is only in the range of 1-100 μg per 1 kg of the fresh cell weight.

The present invention has been made with the foregoing problems of conventional methods in view.

In accordance with one aspect of the present invention, there is provided a method of producing a brassinosteroid, wherein crown gall cells capable of producing the brassinosteroid are cultured in a culture medium, characterized in that said culture is performed in the presence of a cultivation aid selected from the group consisting of auxins, sterols, squalene, casamino acid and mixtures thereof.

In another aspect, the present invention provides a method of producing a brassinosteroid, wherein crown gall cells capable of producing the brassinosteroid are cultured in a culture medium, characterized in that said culture is performed while irradiating said culture medium with a light of a wavelength within the range of 580-900 nm.

The present invention will now be described in detail below.

The crown gall cells to be used in the present invention may be obtained by any known method. A typical method for the production of crown gall cells includes infecting plant cells capable of producing a desired brassinosteroid with a plant tumor inducing bacterium to introduce part of plasmids of the bacterium into the plant cells and thereby to transform the plant cells therewith. Examples of suitable plant tumor inducing bacteria include those belonging to Aqrobacterium. Examples of suitable plant cells to be transformed include dicotyledons, such as *Catharanthus roseus, Nicotiana tabacum, Helianthus tuberosus, Helianthus annuus, Brassica rapa, Bellis perennis* and *Kalanchoe daigremontiana*, and part of monocotyledons such as liliaceae, araceae and gramineae.

The transformant (crown gall cells) is cultured in a culture medium in the presence of a cultivation aid to induce the production of brassinosteroids.

An auxin, a sterol, squalene, casamino acid or a mixture thereof is used as the cultivation aid. Illustrative of suitable auxins are 2,4-dichlorophenoxyacetic acid, indole-3-acetic acid, 1-naphthaleneacetic acid, 4-chloroindole-3-acetic acid, phenylacetic acid, 2,4,5-trichlorophenoxyacetic acid, 2,3,6-trichlorobenzoic acid and 2-naphthoxyacetic acid. Illustrative of suitable sterols (steroid alcohols) are cholesterol, desmosterol, zymosterol and lanosterol.

It is known that crown gall cells can produce by themselves auxins and cytokinins required for their proliferation. It has been, therefore, considered to be unnecessary to add a plant growth hormone to a culture medium in which crown gall cells are to be cultivated. The fact that the addition of the above cultivation aid to a culture medium in which crown gall cells are cultured can remarkably accelerate the production of brassinosteroids is accordingly not expected.

As the culture medium, there may be used, for example, Murashige-Skoog medium (MS medium), Gamborg medium, Nitsch and Nitsch medium and Heller medium.

The cultivation aid is used in an amount effective to facilitate the production of brassinosteroids. The amount of the cultivation aid varies with the kind thereof. Thus, auxins are generally used in an amount of 0.01-100 mg, preferably 0.1-10 mg, per liter of the culture medium. Sterols and squalene are generally used in an amount of 0.1-1000 mg, preferably 1-100 mg, per liter of the culture medium. Casamino acid is generally used in an amount of 0.1-100 g, preferably 0.1-10 g, per liter of the culture medium.

The cultivation aid may be added to the culture medium at the start of the cultivation of the crown gall cells or at a later stage of the cultivation. It is preferable to add the cultivation aid to the culture medium after the cell growth has reached to the logarithmic phase. When the cultivation aid used has a tendency to inhibit the initial growth of the crown gall, it is recommendable to incorporate the cultivation aid after the cell growth has reached to the logarithmic phase.

The culture of the crown gall cells may be performed under conditions conventionally adopted for the cultivation of plant cells. Generally, the culture is carried out at a temperature of 24°-34 ° C. with shaking for a period of time sufficient to proliferate the cells to a desired degree.

It is preferred that the cultivation of the crown gall cells be performed while irradiating the culture medium with a light of a wavelength within the range of 580-900 nm for reasons of improving the yield of the brassinosteroids. In this case, it is desirable not to irradiate a light of a wavelength within the range of 560 nm or less, especially 500 nm or less, though the presence of a light of a wavelength of over 900 nm does not adversly affect the production of brassinosteroids. Thus, the irradiation is suitably performed with the use of a white light through a masking film adapted to block a light of a wavelength of 500 nm or less, preferably 560 nm or less. Red light, orange light or yellow light is suitably used.

After cultivation, the brassinosteroid or brassinosteroids are recovered from the culture by any known manner. For example, the culture is homogenized to disrupt the cells. The resulting mixture is then extracted with a suitable solvent such as methanol or chloroform and the extract is subjected to separation and purification treatments by, for example, chromatography.

The following examples will further illustrate the present invention.

REFERENCE EXAMPLE

Preparation of Crown Gall Cells

A strain of Agrobacterium tumefaciens A 208 was incubated for 16 hours on a nutrient broth agar to form colonies. These colonies were collected and inoculated on portions of the stems of Catharanthus roseus seedlings (stem length: 15–20 cm) which portions had been scratched with a surgical knife. The seedlings were then allowed to grow at 27°–28° C. in a greenhouse for 1 month. As a result, tumors (crown galls) with a diameter of about 1 cm were formed on the inoculated portions. The crown galls were collected and the outer surfaces thereof were sterilized with a 10% bleaching solution. An about 3 mm cube was cut from the inside portion of each crown gall and was subjected to shaking culture at 26° C. and 100 rpm in the dark in the following MS liquid culture medium containing antibiotics (200 mg per liter of carbenicillin and 100 mg per liter of vancomycin):

| Composition of MS Culture Medium | |
|---|---|
| Ingredient | Content (mg per liter) |
| $MgSO_4.7H_2O$ | 370 |
| $CaCl_2.2H_2O$ | 440 |
| $KNO_3$ | 1900 |
| $NH_4NO_3$ | 1650 |
| $KH_2PO_4$ | 170 |
| $FeSO_4.7H_2O$ | 27.8 |
| $Na_2EDTA$ | 37.3 |
| $MnSO_4.4H_2O$ | 22.3 |
| $ZnSO_4.7H_2O$ | 8.6 |
| $CuSO_4.5H_2O$ | 0.024 |
| $CoCl_2.6H_2O$ | 0.025 |
| KI | 0.83 |
| $H_3BO_3$ | 6.2 |
| $Na_2MoO_4.2H_2O$ | 0.25 |
| Sucrose | 30000 |
| myo-Inositol | 100 |
| Nicotinic acid | 0.5 |
| Pyridoxine hydrochloride | 0.5 |
| Thiamin hydrochloride | 0.1 |
| Glycine | 2 |

The proliferated cells were then collected in an aseptic liquid culture medium. This was then transferred to an MS agar culture medium constituted of the above MS culture medium and 2% agar. The cells V208 rapidly grew on this culture medium. Passage culture of V208 cells was performed using the similar agar culture medium in every 20 days. The resulting V208 cells were subsequently transferred to MS liquid culture medium and passage culture with shaking was performed in every week, thereby to obtain suspended cells of V208 (hereinafter referred to as VNC'cells). The VNC' cells were found to produce brassinosteroids (mainly brassinolide and castasterone) in a stable manner and the producibility thereof remained unchanged through 1 year passage culture.

EXAMPLE 1

The crown gall cell lines VNC' of Catharanthus roseus obtained in Reference Example were cultured in seven 500 ml conical flasks respectively containing 150 ml of MS culture medium (pH: 6.7) and 0, 0.1, 0.5, 1, 5, 10 and 50 mg per 1 liter of the culture medium of 2,4-dichloro-phenoxyacetic acid (hereinafter referred to as 2,4-D) on a reciprocal shaker (100 rpm) at 27° C. in the dark for 14 days. Then, the culture in each of the flasks was filtered into a cell fraction (C) and a filtrate (F).

The cells (C) thus collected (about 50 g) were homogenized with 200 ml of methanol and homegenized mixture was filtered through a glass filter. The above homogenization-extraction operation was repeated three times in total to obtain a methanol extract. The methanol extract was concentrated in vacuo to obtain about 40 ml of an aqueous concentrate which was rendered alkaline by addition of 0.3 g of sodium hydrogencarbonate. This was then extracted three times with 40 ml of ethyl acetate. After being dried over anhydrous sodium sulfate, the ethyl acetate extract was concentrated in vacuo to obtain a neutral, ethyl acetate fraction (NEc) from the cells (C).

The filtrate (F) separated from the culture (about 100 ml) was rendered alkaline by addition of 0.5 g of sodium hydrogencarbonate and extracted 3 times with ethyl acetate. The extract was dried over anhydrous sodium sulfate and concentrated in vacuo to obtain a neutral, ethyl acetate fraction (NEf) from the filtrate (F).

The both fractions (NEc) and (NEf) were subjected to rice lamina inclination test for the determination of the content of brassinosteroids (BS content). The BS content is determined by comparing the activity of test samples with that of a brassinolide (BL) sample used as standard. The results are shown in Table 1. GC-MS analysis reveals that the brassinosteroids obtain in Example 1 include brassinolide and castasterone.

TABLE 1

| Amount of 2,4-D | 0 | 0.1 | 0.5 | 1 | 5 | 10 | 50 |
|---|---|---|---|---|---|---|---|
| Fresh Weight of Cells (g/flask) | 31 | 20 | 18 | 15 | 7 | 7 | 5 |
| BS Content of NEc (ng BL equivalent/ fresh weight) | 3 | 12 | 40 | 30 | 110 | 120 | 40 |
| BS Content of NEf (ng BL equivalent/ flask) | 10 | 8 | 10 | 25 | 20 | 10 | 10 |

EXAMPLE 2

Example 1 was repeated in the same manner as described except that 2,4-D was not initially added. Thus, the crown gall cell lines VNC' of Catharanthus roseus obtained in Reference Example were cultured in seven 500 ml conical flasks each containing 150 ml of MS culture medium (pH: 6.7) on a reciprocal shaker (100 ml) at 27° C. in the dark. After 10 days from the start of the cultivation, aqueous solutions of 2,4-D were added to respective flasks in amounts so as to provide 2,4-D concentrations of 0.1, 0.5, 1, 5, 10 and 50 mg per 1 liter of the culture medium, and the cultivation was continued for 4 days The BS contents in NEc and NEf are shown in Table 2.

TABLE 2

| Amount of 2,4-D | 0 | 0.1 | 0.5 | 1 | 5 | 10 | 50 |
|---|---|---|---|---|---|---|---|
| Fresh Weight of Cells (g/flask) | 31 | 23 | 24 | 25 | 25 | 19 | 10 |

TABLE 2-continued

| | | | | | | | |
|---|---|---|---|---|---|---|---|
| BS Content of NEc (ng BL equivalent/ fresh weight) | 3 | 10 | 50 | 12 | 100 | 500 | 100 |
| BS Content of NEf (ng BL equivalent/ flask) | 10 | 8 | 40 | 50 | 40 | 25 | 25 |

From the results shown in Tables 1 and 2, it is seen that the addition of 2,4-D is effective in promoting the production of BS. Especially, when 2,4-D is added after the cells have been proliferated, the effect is very remarkable. Similar results are found to be obtained when 3-indolylacetic acid and 1-naphthyl-acetic acid are each used in place of 2,4-D.

EXAMPLE 3

Example 2 was repeated in the same manner as described except that cholesterol was used in place of 2,4-D and added in an amount of 100 mg per 1 liter of the culture medium. The results are summarized in Table 3.

TABLE 3

| Amount of Cholesterol | 0 | 100 |
|---|---|---|
| Fresh Weight of Cells (g/flask) | 45 | 49 |
| BS Content of NEc (ng BL equivalent/ fresh weight) | 2 | 10 |
| BS Content of NEf (ng BL equivalent/ flask) | 5 | 15 |

EXAMPLE 4

Example 2 was repeated in the same manner as described except that squalene was used in place of 2,4-D and added in an amount of 100 mg per 1 liter of the culture medium. The results are summarized in Table 4.

TABLE 4

| Amount of Squalene | 0 | 100 |
|---|---|---|
| Fresh Weight of Cells (g/flask) | 45 | 45 |
| BS Content of NEc (ng BL equivalent/ fresh weight) | 2 | 30 |
| BS Content of NEf (ng BL equivalent/ flask) | 5 | 50 |

EXAMPLE 5

Example 1 was repeated in the same manner as described except that casamino acid was substituted for 2,4-D and was used in amount of 0.07, 0.7 and 7 g per liter of the culture medium. The BS contents in NEc and NEf are shown in Table 5.

TABLE 5

| Amount of Casamino Acid | 0 | 0.07 | 0.7 | 7 |
|---|---|---|---|---|
| Fresh Weight of Cells (g/flask) | 45 | 46 | 45 | 48 |
| BS Content of NEc (ng BL equivalent/ fresh weight) | 2 | 2 | 2 | 11 |
| BS Content of NEf (ng BL equivalent/ flask) | 1 | 18 | 19 | 3 |

EXAMPLE 6

The crown gall cell lines VNC' of Catharanthus roseus obtained in Reference Example were cultured in five 500 ml conical flasks reach containing 150 ml of MS culture medium (pH: 6.7) on a reciprocal shaker (100 rpm) at 27° C. for 14 days while irradiating the flasks with white light at about 16,000 lux. One of the flasks was covered with a light-shielding aluminum foil while another one was not covered at all. The other three flasks were respectively covered with transparent, red, yellow and blue cellophane films. After 14 days cultivation, the culture in each of the flasks was filtered into a cell fraction (C) and a filtrate (F). The BS contents in NEc and NEf are shown in Table 6.

TABLE 6

| Light Irradiated | Dark | Red Light | Yellow Light | Blue Light | White Light |
|---|---|---|---|---|---|
| Fresh Weight of Cells (g/flask) | 34 | 23 | 26 | 19 | 9 |
| BS Content of NEc (ng BL equivalent/ fresh weight) | 1 | 3 | 6 | 1 | 0.6 |
| BS Content of NEf (ng BL equivalent/ flask) | 1 | 18 | 19 | 3 | 0 |

It is generally known that irradiation of light inhibits the growth of cells. As seen from the results shown above, however, the irradiation of red and yellow light is effective in improving the BS production of crown gall cells.

What is claimed is:

1. A method of producing a brassinosteroid comprising:
   culturing crown gall cells capable of producing the brassinosteroid in a culture medium containing a cultivation aid selected from the group consisting of auxins, sterols, squalene, casamino acid and mixtures thereof, to produce said brassinosteroid; and recovering said brassinosteroid by separating said brassinosteroid from said cells and culture medium.

2. A method as claimed in claim 1, wherein said cultivation aid is at least one auxin selected from 2,4-dichlorophenoxyacetic acid, indole-3-acetic acid and 1-naphthaleneacetic acid.

3. A method as claimed in claim 1, wherein said cultivation aid is added to said culture medium after the cells have been in the logarithmic phase.

4. A method as claimed in claim 1, wherein said culturing is performed while irradiating said culture medium with a light of a wavelength within the range of 580-900 nm.

5. A method of producing a brassinosteroid comprising:
   culturing crown gall cells capable of producing the brassinosteroid in a culture medium while irradiating said culture medium with a light of a wavelength within the range of 590-900 nm, to produce said brassinosteroid; and recovering said brassinosteroid by separating said brassinosteroid from said cells and culture medium.

6. The method of claim 1, wherein said brassinosteroid is separated from said cells by extraction.

7. The method of claim 1 wherein said brassinosteroid is separated from said culture medium by extraction.

8. The method of claim 1 wherein said brassinosteroid is separated from both said cells and said culture medium by extraction.

9. The method of claim 5 wherein said brassinosteroid is separated from said cells by extraction.

10. The method of claim 5 wherein said brassinosteroid is separated from said culture medium by extraction.

11. The method of claim 5 wherein said brassinosteroid is separated from both said cells and said culture medium by extraction.

* * * * *

UNITED STATES PATENT AND TRADEMARK OFFICE
CERTIFICATE OF CORRECTION

PATENT NO. : 5,084,388
DATED : January 28, 1992
INVENTOR(S) : SAIMOTO et al

It is certified that error appears in the above-identified patent and that said Letters Patent is hereby corrected as shown below:

On the Title page, item [73],

"Assignees: Somar Corporation and the Institute of Physical and Chemical Research, both of The Institute of Physical and Chemical Research, Japan" should read --Assignees: Somar Corporation and the Institute of Physical and Chemical Research, both of Japan.--

Col. 1, line 14, ""Brassinosteriod" is a general term of" should read --"Brassinosteriod" is a general term of--;

line 15, "brassinolide and its homologues. Currently know are 22" should read --brassinolide and its homologues. Currently known are 22--; and line 66, "Aqrobacterium" should read --Agrobacterium--.

UNITED STATES PATENT AND TRADEMARK OFFICE
CERTIFICATE OF CORRECTION

PATENT NO. : 5,084,388

DATED : January 28, 1992

INVENTOR(S) : SAIMOTO et al

It is certified that error appears in the above-identified patent and that said Letters Patent is hereby corrected as shown below:

Col. 6, line 1, "Catharanthus" should read --*Catharanthus*--;

line 2, "roseus" should read --*roseus*--.

Signed and Sealed this

Fifteenth Day of June, 1993

Attest:

MICHAEL K. KIRK

Attesting Officer

Acting Commissioner of Patents and Trademarks